US005527293A

United States Patent [19]
Zamierowski

[11] Patent Number: 5,527,293
[45] Date of Patent: Jun. 18, 1996

[54] FASTENING SYSTEM AND METHOD

[75] Inventor: David S. Zamierowski, Shawnee Mission, Kans.

[73] Assignee: Kinetic Concepts, Inc., San Antonio, Tex.

[21] Appl. No.: 152,440

[22] Filed: Nov. 15, 1993

Related U.S. Application Data

[63] Continuation-in-part of Ser. No. 699,936, May 14, 1901, Pat. No. 5,261,893, which is a continuation-in-part of Ser. No. 504,598, Apr. 3, 1990, Pat. No. 5,100,396, which is a continuation-in-part of Ser. No. 332,699, Apr. 3, 1989, Pat. No. 4,969,880.

[51] Int. Cl.⁶ ........................................ A61M 5/32
[52] U.S. Cl. ........................ 604/176; 128/898; 602/46; 602/52; 604/151; 604/290; 604/313
[58] Field of Search ..................... 604/174–176, 604/179, 180, 290, 291, 304, 305, 307, 313, 280, 131, 140, 151; 128/DIG. 26, 898; 602/46, 52, 14

[56] References Cited

U.S. PATENT DOCUMENTS

| Number | Date | Name | Ref |
|---|---|---|---|
| 1,355,846 | 10/1920 | Rannells . | |
| 2,547,758 | 4/1951 | Keeling . | |
| 2,969,057 | 1/1961 | Simmons . | |
| 3,367,332 | 2/1968 | Groves . | |
| 3,648,692 | 3/1972 | Wheeler | 602/46 |
| 3,682,180 | 8/1972 | McFarlane . | |
| 3,826,254 | 7/1974 | Mellor . | |
| 4,080,970 | 3/1978 | Miller . | |
| 4,096,853 | 6/1978 | Weigand . | |
| 4,139,004 | 2/1979 | Gonzalez | 602/14 |
| 4,165,748 | 8/1979 | Johnson . | |
| 4,261,363 | 4/1981 | Russo . | |
| 4,275,721 | 6/1981 | Olson . | |
| 4,297,995 | 11/1981 | Golub . | |
| 4,333,468 | 6/1982 | Geist . | |
| 4,373,519 | 2/1983 | Errede et al. . | |
| 4,382,441 | 5/1983 | Svedman . | |
| 4,392,853 | 7/1983 | Muto . | |
| 4,419,097 | 12/1983 | Rowland . | |
| 4,475,909 | 10/1984 | Eisenberg . | |
| 4,480,638 | 11/1984 | Schmid . | |
| 4,525,166 | 6/1985 | Leclerc . | |
| 4,540,412 | 9/1985 | Van Overloop . | |
| 4,543,100 | 9/1985 | Brodsky . | |
| 4,551,139 | 11/1985 | Plaas et al. | 604/290 |
| 4,569,348 | 2/1986 | Hasslinger . | |
| 4,605,399 | 8/1986 | Weston et al. . | |
| 4,608,041 | 8/1986 | Nielsen . | |
| 4,640,688 | 2/1987 | Hauser . | |
| 4,733,659 | 3/1988 | Edenbaum et al. | 602/46 |
| 4,743,232 | 5/1988 | Kruger . | |
| 4,838,883 | 6/1989 | Matsuura . | |
| 4,840,187 | 6/1989 | Brazier . | |
| 4,863,449 | 9/1989 | Therriault et al. . | |
| 4,872,450 | 10/1989 | Austad | 602/46 |
| 4,878,901 | 11/1989 | Sachse . | |
| 4,897,081 | 1/1990 | Poirier et al. . | |
| 4,906,233 | 3/1990 | Moriuchi et al. . | |
| 4,906,240 | 3/1990 | Reed et al. | 602/46 |
| 4,919,654 | 4/1990 | Kalt . | |
| 4,941,882 | 7/1990 | Ward et al. . | |
| 4,953,565 | 9/1990 | Tachibana et al. . | |
| 4,969,880 | 11/1990 | Zamierowski . | |
| 4,985,019 | 1/1991 | Michelson . | |
| 5,037,397 | 8/1991 | Kalt et al. . | |
| 5,100,396 | 3/1992 | Zamierowski . | |
| 5,149,331 | 9/1992 | Ferdman et al. | 604/290 |
| 5,261,893 | 11/1993 | Zamierowski . | |
| 5,298,015 | 3/1994 | Komatsuzaki et al. | 602/46 |

FOREIGN PATENT DOCUMENTS

| | | | |
|---|---|---|---|
| 0100148 | 2/1984 | European Pat. Off. | 602/46 |
| 2750592 | 5/1978 | Germany | 602/46 |

Primary Examiner—C. Fred Rosenbaum
Assistant Examiner—Chalin Smith
Attorney, Agent, or Firm—Litman, McMahon and Brown

[57] ABSTRACT

A fastening system includes a membrane assembly which can comprise a pair of body panels secured together at a seam. The membrane panels can comprise a semi-permeable material. A sheath assembly has a tubular configuration with proximate and distal ends and a sheath passage extending therebetween. The sheath assembly can be fastened to the membrane assembly by adhesively securing the sheath assembly adjacent to its proximate end between the mem- brane panels at the membrane assembly seam. A sheath-to-tube fastener is provided for fastening the sheath assembly to a tube. In one embodiment of the present invention a surgical sponge is fastened to the membranes in fluidic connection with the sheath, which is fastened to a suction tube for drawing blood from a surgical site. A method of treating surface wounds such as burns, pressure ulcers and skin graft donor sites comprises the steps of applying a dressing including a foam section to the wound, adhesively applying a polymer sheet to the foam section, connecting a suction tube to with the foam section, applying negative pressure to the wound through the section tube by use of a motorized pump and directing fluid from the surface wound through the foam section by the polymer sheet.

1 Claim, 6 Drawing Sheets

FASTENING SYSTEM AND METHOD

Continuation-in-Part of U.S. Ser. No. 699,936, filed May 14, 1991, now U.S. Pat. No. 5,261,893, which is a Continuation-in-Part of U.S. Ser. No. 504,598, filed Apr. 3, 1990, now U.S. Pat. No. 5,100,396, which is a Continuation-in Part of U.S. Ser. No. 332,699, filed Apr. 3, 1989, now U.S. Pat. No. 4,969,880.

BACKGROUND OF THE INVENTION

1. Field of the Invention

The present invention relates generally to fastening systems, and in particular to a system and method for fastening tubes to patients.

2. Description of the Related Art

Various fastening systems and methods have heretofore been devised for meeting the requirements of particular applications. For example, in the medical field, a variety of fastening systems are employed in connection with various medical procedures. Previous medical fastening systems include sutures, clamps, belts, ties, adhesive tape and other tapes. Common medical fastening procedures include fastening tubes to patients.

Medical patients are intubated in connection with a number of common medical procedures. For example, nasogastric tubes are inserted into the patient's stomach via a nostril for aspirating the stomach contents. Tubes are commonly inserted through stomal openings, e.g., in connection with ileostomies, gastrostomies, etc.

Intravenous (IV) tubing, catheters, fiber optic cables and electrical wire leads from electrodes all present problems associated with fastening tubes, cables and leads to patients. Frequently, a tube-to-patient connection with some structural integrity is desired, i.e., to reduce the risk of injury from the tube being torn loose from the patient. Since considerable tensile force can be exerted on such tubing (e.g., by an intubated patient rolling over in bed), previous solutions such as secure taping with strong adhesive tape have been utilized with some success. However, there are disadvantages associated with the prolonged application of adhesive tape. Since many types of adhesive tape used for medical applications are relatively impervious, skin covered thereby is susceptible to maceration and the formation of milia consisting of inflamed hair follicles and glands.

Tubes and other flexible lines can also be sutured to patients, but there are disadvantages associated with this technique. For example, the sutures can be uncomfortable to the patient, and can cause infection, inflammation and scaring.

Improved patient comfort can be achieved by applying semi-permeable membranes, which tend to be permeable to vapors, to wound sites. Such membranes are available from several companies, including: "Polyskin" from Kendall Health Care Products Company; "Opsite" from Smith & Nephew, Inc.; "Bioclusive" from Johnson & Johnson Products, Inc.; and "Tegaderm" from 3M Health Care. Such membranes commonly have adhesive faces for adhesion to patient's skin, but are normally relatively thin with little structural integrity. Thus, for all of their patient comfort advantages, the semipermeable membranes are often not a satisfactory substitute for adhesive tape.

Tapes are also available which have permeable characteristics, but many of them lack sufficient structural integrity for practical use as the sole and exclusive fastening system for tubes and other flexible lines.

However, the semi-permeable membrane materials referred to above can be combined with other, stronger materials, such as flexible plastic tubing, to provide wound dressings with considerable advantages over previous, conventional gauze-and-tape dressings. The Zamierowski U.S. Pat. No. 4,969,880 discloses such a wound dressing which effectively exploits the combined advantages of semi-permeable membranes and flexible plastic tubing.

The applicability of such a combination to a variety of fastening applications is addressed by the present invention.

Another problem commonly encountered in medical surgical procedures relates to the evacuation of blood from the operating site. Devices have been provided for capturing the blood and other fluids, e.g., eye drains available from Merocel Corporation which are fastened to patient's cheeks during ophthalmologic procedures. Sponges and gauze are often used for evacuating blood and other fluids from operating sites. Suction tubes are also utilized, e.g., with cannulae, and can be provided with small sponge attachments on their ends for gathering fluid, e.g. Tebbett's suction pads available from Dow Corning. The present invention can be utilized as a device for fastening and fluidically communicating surgical sponges with suction for the collection of blood and other fluids during surgery, which can reduce the need for handling and weighing blood-saturated sponges in the operating room, which is frequently required at present to determine a volume of blood replacement required for a patient during surgery.

SUMMARY OF THE INVENTION

In the practice of the present invention, a fastening system and method are provided for fastening a variety of tubes to patients for performing various medical procedures thereon. The fastening system can comprise a membrane assembly consisting of a pair of membrane body panels adhesively joined at a seam extending transversely across the membrane assembly. The membrane assembly can comprise a semipermeable material with an adhesive face covered by an adhesive backing prior to use. A sheath assembly includes proximate and distal ends and a sheath passage extending therebetween. The sheath assembly is fastened to the membrane assembly by extending the sheath assembly between the body panels at the membrane assembly seam in proximity to the sheath assembly proximate end, which can be split to form a pair of sheath proximate end tabs. A sheath-to-tube fastener is provided for fastening the sheath to a tube inserted in the patient. The fastening system can also mount the sheath adjacent to an end edge thereof, for example in a fastening system construction particularly designed for fastening a nasogastric tube to a patient. A surgical suction fastening system is also disclosed wherein a sponge is sandwiched between the panels of the membrane assembly with a portion of the sponge extending beyond a membrane assembly for drawing fluids, e.g., blood from a surgical site. Methods of fastening the present invention in connection with various medical procedures are further disclosed, particularly those involving intubation of a patient, e.g., nasogastric, suction, intravenous, Foley catheter, stomal and percutaneous tubing.

Another method in the practice of the present invention involves sandwiching a surgical sponge between the membrane assembly panels and fastening the sheath to a suction tube for suction evacuating blood from an operating site.

OBJECTS AND ADVANTAGES OF THE INVENTION

The principle objects and advantages of the present invention include: providing a fastening system and method, providing such a fastening system and method which are particularly well-adapted for medical applications; providing such a system and method for fastening tubing to a medical patient; providing such a system and method for fastening a surgical sponge to a suction source in fluidic communication; providing such a system and method which have considerable structural strength; providing such a system and method which are relatively comfortable to patients; providing such a system and method which can reduce or minimize maceration and the formation of milia as compared to adhesive tape systems and methods; providing such a system and method which allow a wide variety of applications with a common device; providing such a device and method which can help control nosocomial and other infections; and providing such a device and method which are efficient in operation, economical to manufacture and practice, and are particularly well designed for the proposed usages thereof.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 2a is a plan view of a fastening system for a nasogastric tube comprising a first modified or alternative embodiment of the present invention.

FIG. 3a is an enlarged, fragmentary, cross-sectional view thereof taken generally along 3a—3a in FIG. 2a.

FIG. 13 is a cross-sectional view of a fastening system comprising a third modified or alternative embodiment of the present invention, shown fastening an intravenous tube to a patient.

DETAILED DESCRIPTION OF THE PREFERRED EMBODIMENTS

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. Said terminology will include the words specifically mentioned, derivatives thereof and words of a similar import.

II. Nasogastric Tube Fastening System 2

Figure 1:
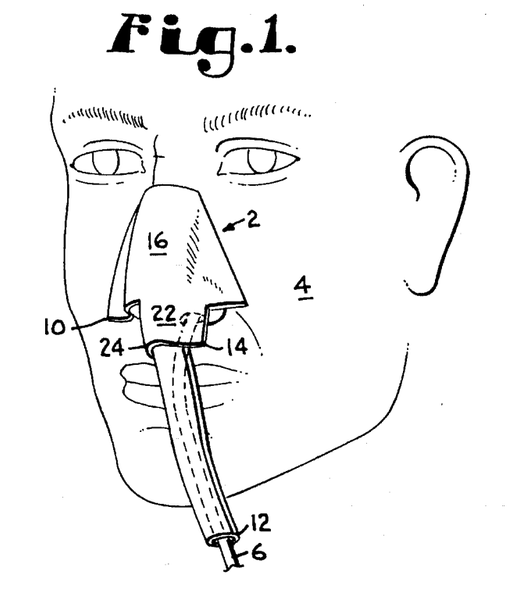
FIG. 1 is a perspective view of a fastening system embodying the present invention, shown fastening a nasogastric tube.

Referring to the drawing in more detail, the reference numeral 2 generally designates a medical fastening system which embodies the present invention. Without limitations on the generality of useful applications of the medical fastening system 2, it is shown applied to a medical patient's face 4 attaching a nasogastric tube 6, which is inserted through a nostril 8 of the patient for aspirating the stomach contents.

The fastening system 2 generally comprises a membrane assembly 10, a sheath assembly 12, and a sheath-to-tube fastener 14.

Figure 2:
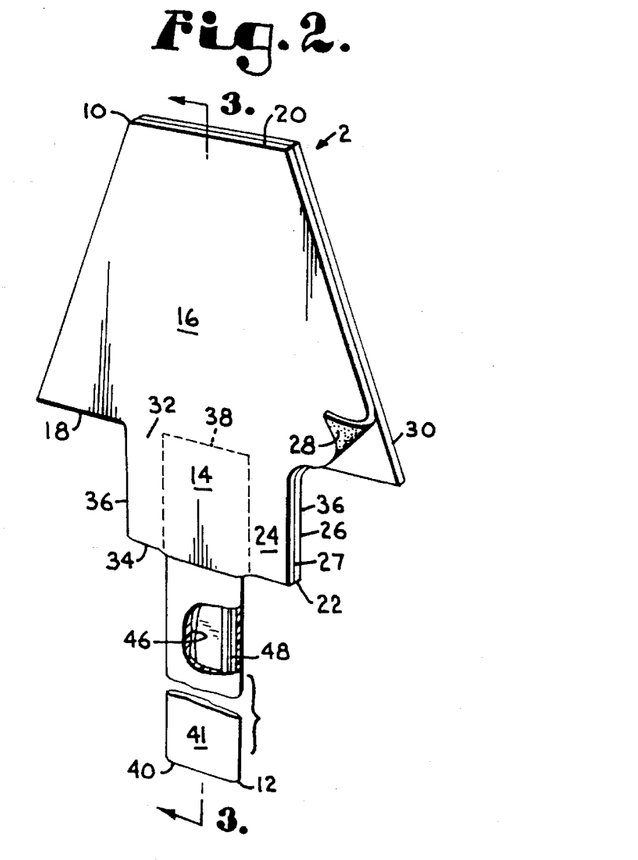
FIG. 2 is an enlarged, perspective view of the fastening system, shown prior to application to a patient.

The membrane assembly 10 includes a first body panel 16 with first and second end edges 18, 19 and opposite side edges 20. A membrane flap or extension 22 extends from the first end edge 18 and includes a first flap panel 24, which can be integral with the body panel 16, and a second flap or body panel 26. The body panel 16 includes an adhesive layer 28 which can be covered by an adhesive backing 30.

The body panel 16 and the flap panels 24, 26 can comprise a vapor-permeable, transparent, polyurethane film material of the type which is available from a number of manufacturers, e.g.: "Tegaderm" dressing from the 3M Company; "Bioclusive" dressing from Johnson & Johnson Products, Inc.; "OpSite" dressing from Smith & Nephew Inc.; and "Polyskin" dressing from Kendall Health Care Products, Inc.

Figures 3, 6, 7, 10:
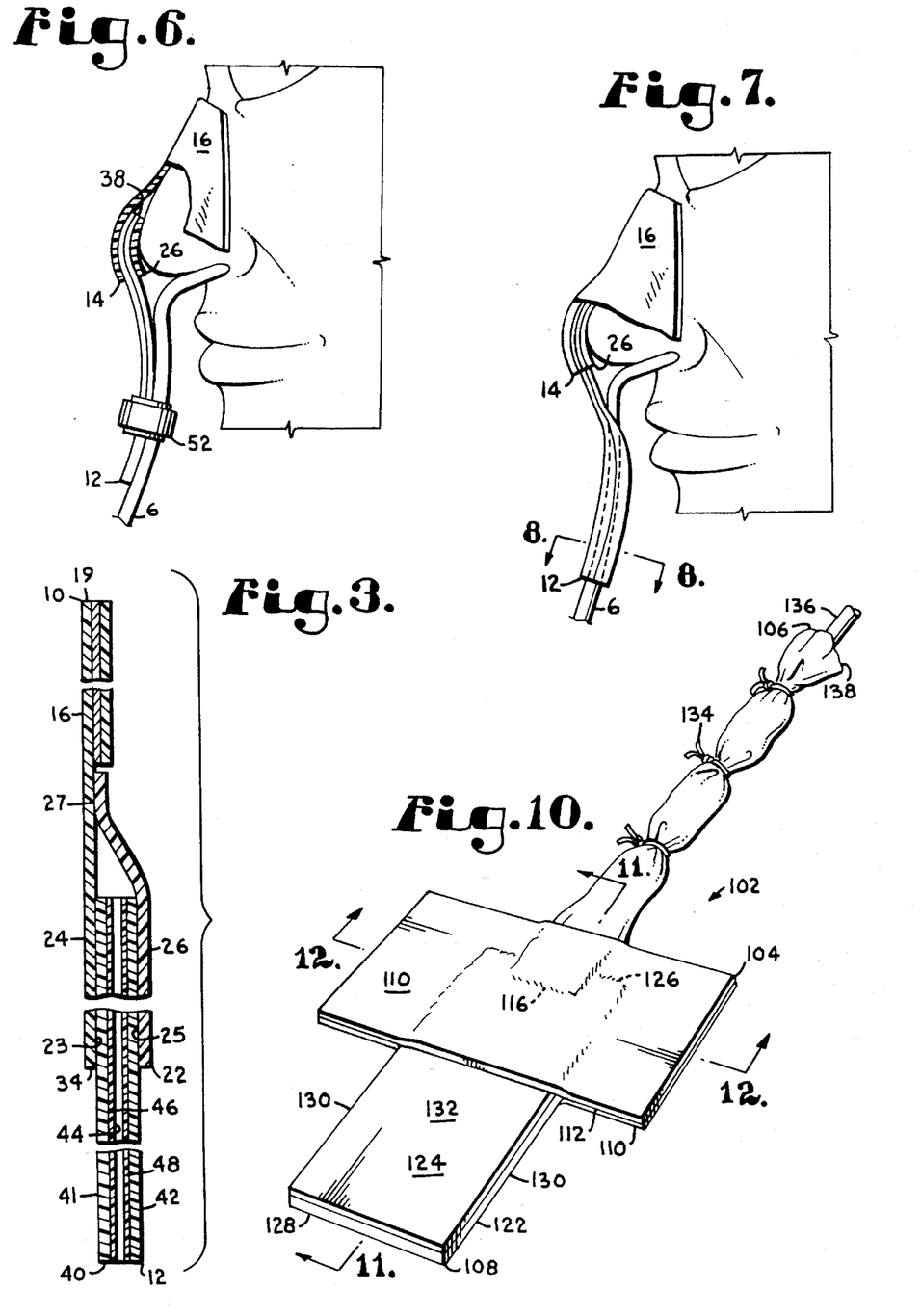
FIG. 3 is an enlarged, fragmentary, cross-sectional view of the fastening system, taken generally line 3—3 in FIG. 2.
FIG. 6 is a side elevational view of the fastening system, showing the nasogastric tube partially within a sheath thereof.
FIG. 7 is an enlarged cross-sectional view of the fastening system, taken generally along line 7—7 in FIG. 6.
FIG. 10 is a perspective view of a fastening system for a surgical sponge comprising a second modified or alternative embodiment of the present invention.

The flap or extension 22 includes a proximate edge 32 connected to the body first end edge, a distal edge 34, opposite side edges 36 and an adhesive seam 27 between adhesive layers 23, 25 on the first and second flap panels 24, 26.

The sheath assembly 12 includes proximate and distal ends 38, 40 with first and second sheath faces 41, 42 each having an adhesive layer 44 thereon adjacent to a sheath passage 46. An adhesive release strip 48 extends through the sheath passage 46. One or both of the sheath faces 41, 42 can be provided with a tear line or marking 50 for access to the passage 46.

Figure 4:
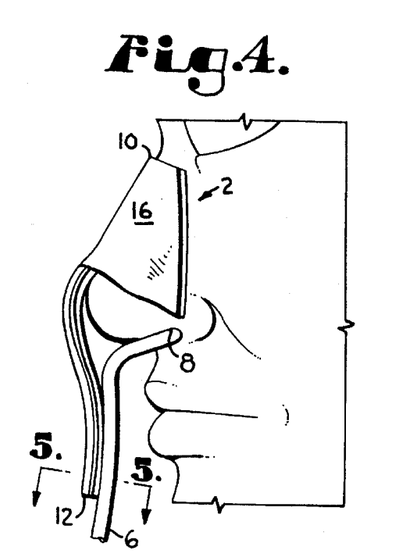
FIG. 4 is a side elevational view of the fastening system.

A method of fastening the nasogastric tube 6 to a patient is disclosed, and includes the steps of pealing away the adhesive backing 30 and adhesively securing the body panel 16 to the nose and/or cheeks of the patient's face 4 (FIGS. 1 and 4).

Figure 5:
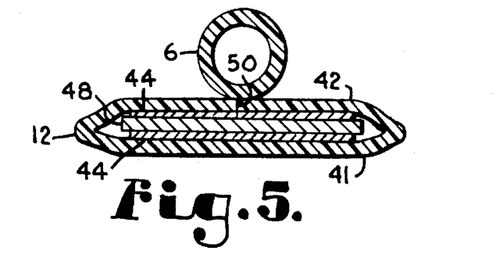
FIG. 5 is an enlarged cross-sectional view of the fastening system taken generally along line 5—5 in FIG. 4.
Figure 9:
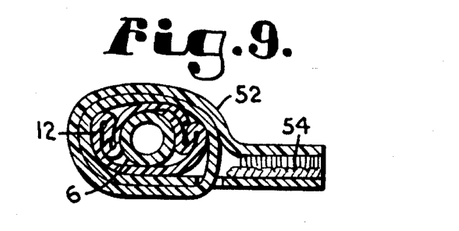
FIG. 9 is an enlarged cross-sectional view of the fastening system taken generally along line 9—9 in FIG. 8.

The flap or extension 22 comprises a double layer of the semi-permeable membrane material with adhesive layers 28 thereof attached at the seam 27 whereby the flap or extension 22 will not adhere to the patient. The sheath assembly 12 can overlie the tube 6, as shown in FIGS. 1, 4 and 5, and can be temporarily secured thereto with a cinch loop fastener 52 as shown in FIG. 6. The cinch loop fastener 52 can include a hook-and-loop fastener 54 for releasably cinching the sheath assembly 12 to the tube 6. Such a fastener is shown in FIG. 9. However, various other sheath-to-tube fastening means could be employed, including twist ties, rubber bands, clips, etc. By employing a releasable fastener 52, the tube 6 can easily be repositioned with respect to the fastening system 2. The position of the tube 6 can be confirmed by X-ray examination or by other means, and can be adjusted if necessary.

Figure 8:
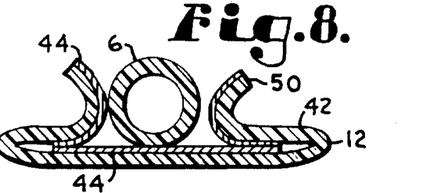
FIG. 8 is a side elevational view of the fastening system, particularly showing the nasogastric tube enclosed within the sheath and secured by a cinch loop fastener.

When the tube 6 is properly positioned, it can be resecured to the fastening system 2 by opening the sheath assembly 12 and placing the tube 6 within the sheath passage 46. The sheath assembly 12 can be opened by cutting it longitudinally, or by tearing it along a tear line 50 to provide access to the passage 46. The adhesive release strip 48 can then be removed from the sheath assembly 12 and the tube 6 placed in the passage 46 as shown in FIG. 8. The sheath 12 can then be folded over the tube 6 (FIGS. 7 and 9). The tube 6 can be adhesively secured in place by pressing the adhesive layers 44 of the sheath 12 thereagainst. The tube 6 can also be secured within the sheath 12 by the cinch loop fastener 52 (FIG. 9). With the tube 6 thus secured, the tube is relatively securely attached to the patient. Patient comfort is facilitated by the use of the semi-permeable material for the membrane assembly 10, which passes vapors and air for breathability. Thus, as compared to relatively impervious fastening systems (e.g., adhesive tape), greater patient comfort can be achieved and skin problems such as maceration or formulation of milia (gland or hair follicle inflammation accompanied by pustules) can be reduced. Furthermore, the nasal tip and the nostril rim area of the patient can be observed for evidence of inflammation, infection, etc., and can be promptly detected. Furthermore, necrosis of the nostril tip, which often accompanies overly forceful adhesive taping, can be observed and therefore minimized or avoided.

Figures 2A, 3A, 13:
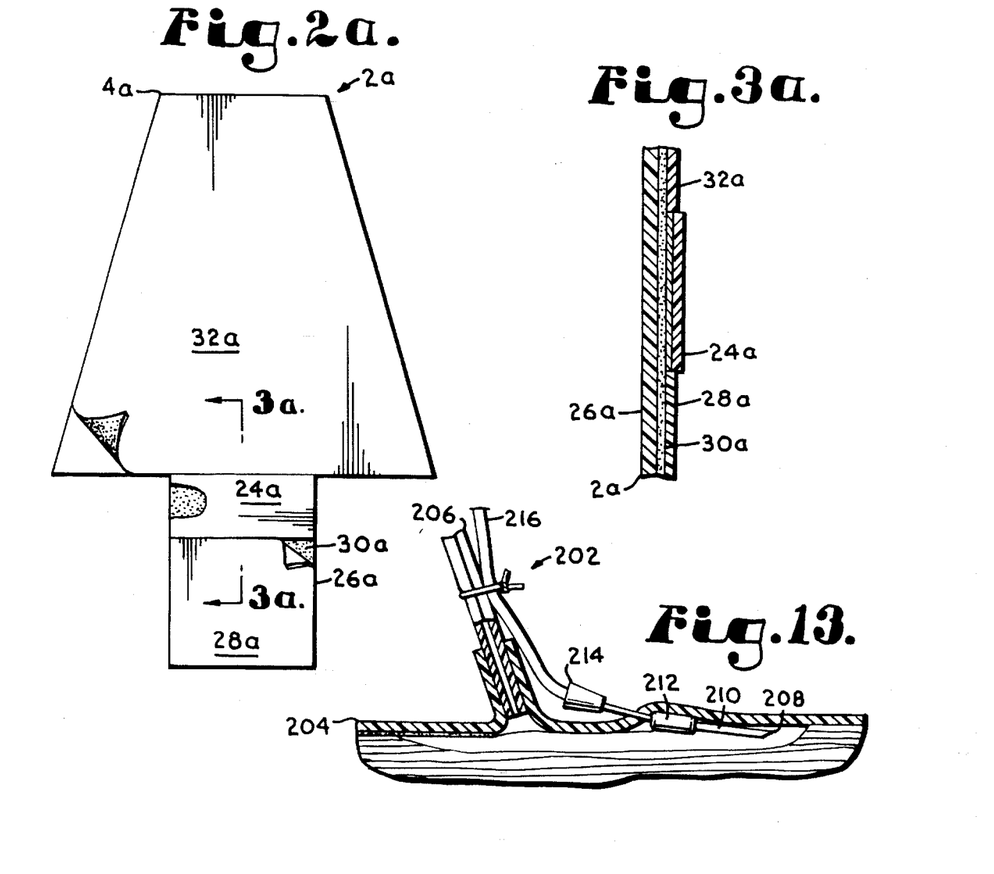

A fastening system 2a comprising a first modified or alternative embodiment of the present invention is shown in FIGS. 2a and 3a. The fastening system 2a is particularly adapted for fastening a nasogastric tube 6, but like the fastening system 2, could also fasten an intravenous tube and other types of tubing and flexible lines. The fastening system 2a includes an intermediate membrane strip 4a adhesively attached to a first flap panel 24a. The first flap panel 24a includes an end portion 26a with adhesive backing layer 28a which can be peeled away for exposing an adhesive layer 30a.

In using the fastening system 2a, a body adhesive backing 32a is peeled away from the membrane 4a to expose the adhesive layer 30a, and the membrane 4a is applied to the patient as described above. The first flap panel 24a is preferably positioned in proximity to the patient's nostrils, and since it does not have any exposed adhesive, the fastening system 2a can be utilized to leave the patient's nostrils clear for breathing. The extension adhesive backing 28a is peeled away to expose the adhesive layer 30a and the membrane end portion 26a can be wrapped around the nasogastric tube 6 for securing same to patient.

III. Suction Fastening System 102

A surgical suction fastening system 102 comprises a second modified or alternative embodiment of the present invention and is shown in FIG. 9. The surgical suction fastening system 102 generally includes a membrane 104, a sheath assembly 106 and a sponge assembly 108. The membrane and sheath assemblies 104, 106 can comprise, for example, a wound dressing as shown in my U.S. patent application Ser. No. 504,598 for fluidic connection system and method, which is co-pending herewith and which is incorporated herein by reference, along with my U.S. Pat. No. 4,969,880.

The membrane assembly 104 comprises a pair of semi-permeable panels 110 which are adhesively joined at a membrane assembly seam 112 whereat a proximate end 114 of the sheath assembly 106 is secured in position. The sheath proximate end 114 forms a split mouth 116 with first and second mouth tabs 118, 120 each positioned adjacent to a respective membrane assembly panel 110.

Figures 11, 12:
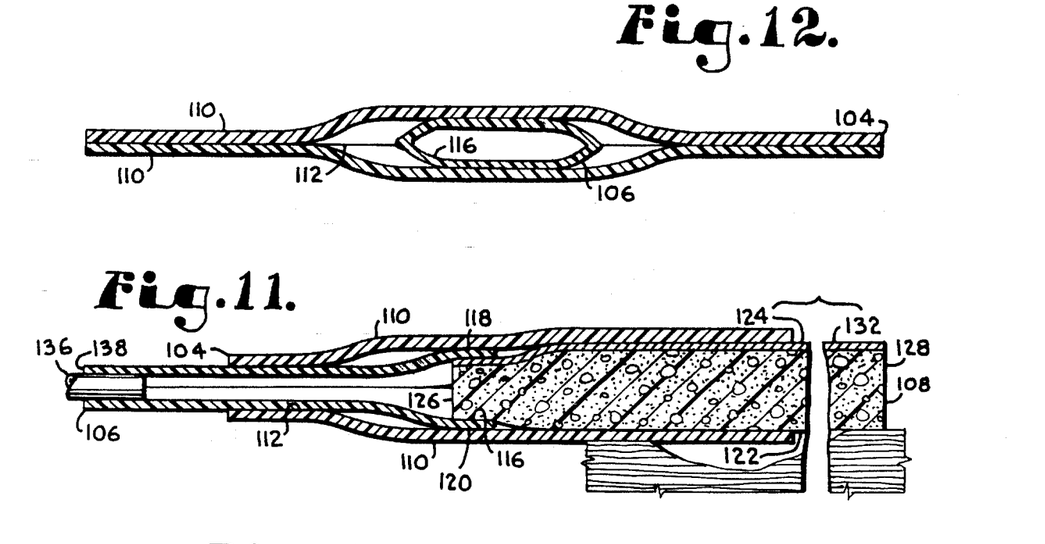
FIG. 11 is an enlarged, fragmentary, cross-sectional view thereof, taken generally along line 11—11 in FIG. 10.
FIG. 12 is an enlarged cross-sectional view thereof taken generally along line 12—12 in FIG. 10.

The sponge 108 includes a first or open face 122 and a second or occluded face 124, proximate and distal ends 126, 128 and opposite side edges 130. A sponge backing material or layer 132 which can cover the second or occluded face 124 of the sponge 108 and can be relatively impervious. As shown in FIG. 11, the sheath split mouth 116 is adapted to receive a portion of the sponge 108 between the mouth tabs 118, 120 adjacent to the sponge proximate end 126.

In operation, the fastening system 102 can be used singly or in multiples to draw blood from an open dissection plane, particularly for the purpose of maintaining a critical point free of blood. The sheath assembly 106 can be attached, e.g., by twist ties 134, to a suction line 136 in an area between a distal end 138 of the sheath assembly 106 and the membrane assembly seam 112. The suction tube 136 can be attached to a suitable suction source (not shown). The membrane assembly 104 can comprise either impervious (e.g., thin, flexible) or semi-permeable material. Exposure to and immersion in blood and other fluids may cause a semi-permeable material to become less permeable, with a corresponding enhancement of the suction capabilities of the system 102.

The membrane, sheath and sponge assemblies 104,106, 108 can be manufactured or preassembled in various configurations. Alternatively, the fastening system 102 can be assembled by the health care practitioner by placing a suitable sponge assembly 108 in a premanufactured membrane assembly 104 and sheath assembly 106, which could be similar to my fluidic connection system disclosed in my U.S. patent application Ser. No. 504,598 referred to above. Preferably the material comprising the sponge 108 is resistant to shredding and strong enough to not break apart or disintegrate in the wound or operating site. The sponge 108 could be threaded with a radio-opaque thread (e.g., where the membrane assembly panels 110 are joined to the sponge 108 in a middle area thereof) to provide greater structural integrity and also to facilitate detection by X-ray if the sponge were lost in the wound. By providing transparent, or at least translucent, membrane assembly panels 110 and a sheath assembly 106, the movement of blood through the system 102 can be observed. Furthermore, an anti-clotting coating can be provided on the sponge 108 to facilitate efficiency. It is anticipated that most of the blood and fluid would enter the sponge 108 through the exposed area of the first or open face 122 of the sponge 108 through the exposed portions of the sponge side edges 130, and through the sponge distal end 128. However, the sponge 108 could be provided without a backing material or layer 132 for suction through its second face 124.

The sheath assembly 106 preferably is relatively flexible for mobility of the fastening system 102. The sheath assembly 106 can be prevented from collapsing under the suction force by providing it with permanent, crimped edges. Foldable, flat sheathing is available from Aero International, Inc. of Reading, Penn. Alternatively, the sheath assembly 106 can have longitudinal ridges for providing resistance to collapse. The sheath assembly 106 can have a length of about eighteen inches to twenty-six inches for many uses, but its length is practically unlimited. Various connector devices can be used for attachment to the sheath assembly 106, such as a male adapter, which is sometime referred to as a "Christmas tree" for insertions in standard suction tubing, or a "suction block" for allowing multiple fastening systems 102 to be connected to a common suction source. Rubber bands, O-rings, tape and other fastening systems can be used for the sheath-to-tube fastening means. Suction devices such as those commonly used in tonsillectomies can be employed. The blood and fluid connected through the fastening system 102 can be collected remote from the patient for measurement to determine how much, if any, fluid is to be replaced in the patient.

IV. Intravenous Tube Fastening System 202

An intravenous ("IV") tube fastening system 202 comprising a third modified or alternative embodiment of the present invention is shown in FIG. 13. A membrane assembly 204 and a sheath assembly 206 can be substantially the same as the membrane and sheath assemblies 104,106 described above in connection with the surgical suction fastening system 102.

The IV tube fastening system 202 can be applied over an IV site or a cannula 208 inserted into the vein of the patient through a skin puncture site 210. The cannula 108 can be fitted at its distal end with a heparin lock 12 which can lie adjacent to the skin surface.

By forming the membrane assembly 204 of a transparent or translucent material, the heparin lock 212 can be observed through the membrane assembly 204 which overlies it. A hypodermic needle 214 can be inserted through the membrane assembly 204 and into the heparin lock for fluidically connecting an IV tube 216 connected to the needle 214 with the cannula 208 whereby an intravenous flow of fluid can be established. The IV tube 216 can be secured to the sheath assembly 206 by any suitable means including those discussed above. By effectively utilizing the strength, adhesive and vapor permeability properties of the membrane assembly 204 and the sheath assembly 206, the IV puncture site 210 can be effectively closed off against bacteria to reduce the risk of infection, and the IV tube 216 can be effectively secured to the patient to minimize the risk of being inadvertently pulled loose. The semi-permeable nature of the membrane assembly 204 can facilitate patient comfort, particularly if the IV system is left in place for a prolonged period of time. The transparent or translucent nature of the membrane assembly 204 facilitates observation of the puncture site 210, whereby inflation or infection can be promptly detected and treated.

V. Foley Catheter Fastening System 302

Figures 14, 16, 17:
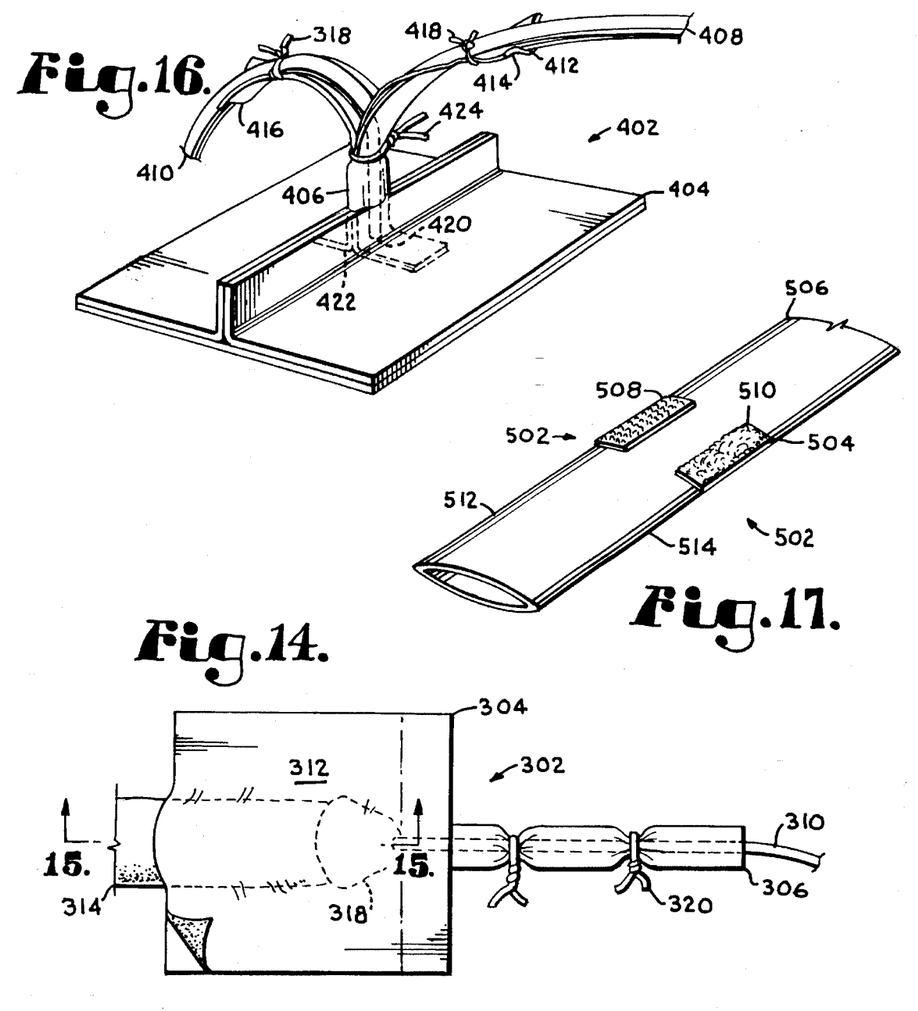
FIG. 14 is a plan view of a fastening system comprising a forth modified or alternative embodiment of the present invention, shown attaching a Foley catheter to a patient.
FIG. 16 is a perspective view of a fastening system comprising a fifth modified or alterative embodiment of the present invention, showing a pair of tubes attached to the fastening system for connection to a patient.
FIG. 17 is a fragmentary, perspective view of a fastening system comprising a sixth modified or alternative embodiment of the present invention, with a hook-and-loop fastener for fastening a sheath.
Figure 15:
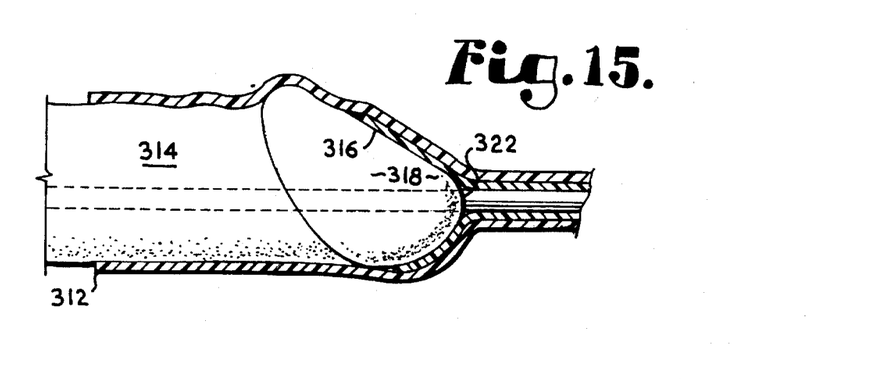
FIG. 15 is an enlarged, fragmentary, cross-sectional view thereof taken generally along line 15—15 in FIG. 14.

A Foley catheter fastening system 302 comprising a fourth modified or alternative embodiment of the present invention is shown in FIGS. 14 and 15, and generally comprises a membrane assembly 304 and a sheath assembly 306, which can be generally similar to the membrane and sheath assemblies described above in connection with the fastening systems 102 and 202.

In the application of the fastening system 302 to a patient, a Foley catheter 308 is applied to the patient by inserting a catheter tube 310 thereof through the urethra and into the bladder of the patient. The tube 310 mounts a balloon on the end thereof which can be inflated with air or liquid in the patient's bladder. The fastening system can be applied by slipping the sheath 306 over the catheter tube 310 and adhesively securing panels 312 of the membrane assembly 304 to the patient's penis 314. Sheath end tabs 316 can be placed on top of and below the glans or penile head 318.

The sheath 306 can be secured to the tube 310 by suitable sheath-to-tube fasteners 320, which can be of any of the types discussed above. The membrane assembly 304 in conjunction with the sheath assembly 306, would enclose the meatal/catheter junction 322 and could be helpful in controlling nosocomial infection entering the urethra through this junction.

Due to the transparent or translucent nature of the membrane assembly 304, the catheter tube 310 can alternatively be inserted after the fastening system 302 is in place by sliding it through the sheath assembly 306 and then into the urethra.

VI. Multiple Tube Fastening System 402

A multiple tube fastening system 402 comprising a fifth modified or alternative embodiment of the present invention is shown FIG. 16 and generally comprises a membrane assembly 404 and a sheath assembly 406, which can be substantially similar to the membrane and sheath assemblies described above in connection with fastening systems 102, 202 and 302. A percutaneous tube 408 and a suction tube 410 extend into the sheath assembly 406 in juxtaposed relation. The sheath assembly 406 can be longitudinally, axially split from a distal end 412 of the sheath assembly 406 to a location in spaced relation from the membrane assembly 404, whereby first and second sheath half-sections 414, 416 are formed. The first sheath half-section 414 can be attached to the percutaneous tube 408 by suitable fastening means 418, and the second sheath half-section 416 can be fastened to the suction tube 410 by similar fastening means 318.

The fastening system 402 can be used in conjunction with a gastrostomy or antrostomy tube 408, with the suction tube 410 provided for draining fluid leakage from around the stomal site. The suction tube 410 can terminate at a proximate end 420 in proximity to a proximate end 422 of the sheath assembly 406. A relatively fluid-tight connection can be formed between the sheath assembly 406 and the tubes 408, 410 with a sheath-to-tube fastening means 424, or adhesive on the inside of the sheath assembly 406, or a combination of both. In this manner irrigation and suction can be applied simultaneously or consecutively without having to remove or disturb the fastening system 402.

Without limitation on the generality of useful applications of the fastening system 402, it is applicable to other surgical procedures such as ileostomy and the placement of ileo conduits, and virtually any other stomal procedures.

Alternatively, the fastening system 402 can include a sheath assembly in the form of a Y-connector or T-connector with supply sources of liquid connected to one branch of the connector and suction sources connected to the branch. Still further, multiple sheath assemblies 406 can be connected to the membrane assembly 404. Tubing and other flexible lines for multiple functions can also be achieved with the fastening system 402 by providing tubing with multiple lumens. Such flexible lines can comprise tubing, electrical wires, e.g., connected to electrodes, fiber optic cables, etc.

VII. Fastening System 502 with Integral Sheath Attachment

A fastening system 502 with an integral sheath clamp 504 is shown in FIG. 17 and comprises a sixth modified or alternative embodiment of the present invention. The fastening system 502 includes a sheath assembly 506 which can otherwise be substantially similar to the sheath assemblies 106, 206, 306 and 406 described above. The integral sheath clamp 504 comprises first and second fastening patches 508, 510 secured to the sheath assembly 506 in proximity to respective opposite second side edges 512, 514 of the sheath assembly 506. The fastening patches 508, 510 can comprise, for example, the hook and loop components of a hook-and-loop fastening system, such as that available under the trademark "VELCRO". Alternatively, the fastening system 502 can comprise other types of mechanical fasteners, such as snaps, etc., or adhesive fasteners. The sheath clamp 504 is particularly useful for temporarily securing a tube to the sheath assembly 506, or as in the step shown in FIG. 6 for temporarily securing a nasogastric tube 6. By including the sheath clamp 504 in the sheath assembly 506, convenience in use can be facilitated because the health care provider does not need to locate a clamping device, which might otherwise be subject to becoming lost or misplaced.

VIII. Wound Dressing System 601

Figure 18:
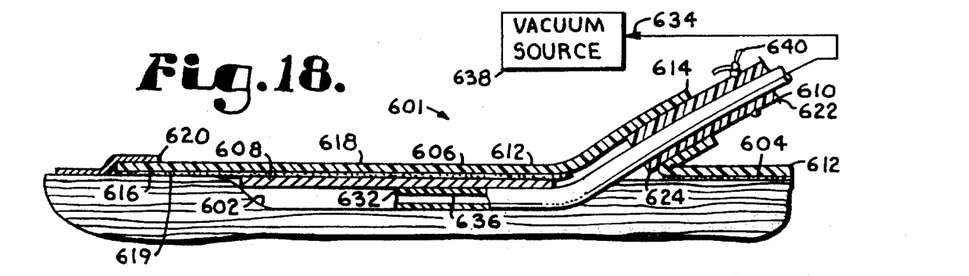
FIG. 18 is a fragmentary, side elevational view of a wound dressing system comprising a seventh modified or alternative embodiment of the present invention.

A wound dressing system comprising a seventh modified or alternative embodiment of the present invention is shown in FIG. 18 and is generally designated by the reference numeral 601. The wound dressing system 601 can be applied to a wound site 602 which is surrounded by healthy skin 604. The dressing system 601 generally consists of panel means 606, fluid control means 608 and conduit means 610.

The panel means 606 can comprise a pair of panel sections 612 joined at a seam 614. The panel sections 612 can comprise a variety of different materials, including semi-permeable membranes such as "Tagaderm", which is available from the 3M (Minnesota Mining and Manufacturing) Company of St. Paul, Minn. The panel sections 612 can also comprise, for example, occlusive, impermeable and impervious films, sheets and layers of various materials which can be chosen for desired characteristics in connection with dressing a particular wound. Such characteristics and criteria might include, for example, permeability, porosity, thickness, flexibility, fluid absorption, hypoallergism, the presence or absence of adhesive coatings, etc. The panel sections have inner and outer surfaces 616, 618. The panel section inner surfaces 616 can be coated with adhesive 619 to provide fixation means for affixing the panel means 606 to the adjacent healthy skin 604 around the perimeter of the wound 602. Adhesive tape 620 can be used as an alternative or supplementary fixation means.

The fluid control means 608 can comprise a variety of materials which can be disposed intermediately between the wound 602 and the panel section inner surfaces 616. Such materials for the fluid control means 608 can include gels such as "Vigilon" primary wound dressing, which is available from C. R. Bard, Inc., Bard Home Health Division, Berkeley Heights, N. J., and membranes such as "Mitraflex" wound dressing, which is available from Calgon Corporation, Subsidiary of Merck & Co., Inc., St. Louis, Mo. The fluid control means can be adapted to meet the requirements of particular wounds 602 being treated. For example, materials can be chosen for their characteristics of permeability or impermeability, absorptive properties and anti-coagulation properties. Hydrophilic and hydrophobic properties can also be important for the fluid control means 608. Various types of mat materials and sponge or foam materials with fluid-wicking properties can be utilized for the fluid control means 608. The properties of the fluid control means 608 preferably compliment the properties of the panel means 606 to provide the desired fluid control for the wound dressing system 601.

The conduit means 310 includes a sheath 322 which can comprise, for example, a sheath such as that which is available from Aero International, Inc., of Reading, Penn. The sheath has a proximate end 624 which is captured within the panel seam 614 and is open at the panel section inner surfaces 616, a distal end 626 located in spaced relation outwardly from the panel section outer surfaces 618, and a sheath passage 628 extending between the sheath ends 624, 626. The sheath distal end 626 has a tapered configuration which converges to a neck opening 627 having a reduced diameter as compared with the rest of the sheath passage 628.

The panel means 606 and the sheath 622 described thus far can be generally similar to any one of several combined panel (or membrane) and sheath systems described in my U.S. Pat. No. 4,969,880 and U.S. Pat. No. 5,100,396, which are incorporated herein by reference.

The conduit means 610 also includes a suction tube 630 with proximate and distal ends 332, 334 and a tube passage 336 extending therebetween. The tube proximate end 332 can be located between the wound 602 and the fluid control means 608, particularly in a system 601 with impervious, hydrophobic fluid control means 608. In such a system the fluid control means 608 would form a fluid barrier, trapping fluid between the wound 602 and the fluid control means 608 for evacuation by the suction tube 630 through its proximate end 632. The tube distal end 634 is connected to a suitable suction or vacuum source 638.

The sheath 622 is provided with means for engaging the suction tube 630 in a fluid-tight gripping engagement. Such means can comprise, for example, one or more encircling ties 640 which can be formed with suture threads, rubber bands, cinch loop fasteners 52 as described herein, etc. Such gripping engagement means can also comprise, for example, the configuration of the sheath distal end 626 with a relatively narrow neck opening 627 and a slightly tapered configuration converging towards the sheath distal end neck opening 627 as described above. This configuration of the sheath distal end 626 permits a tube-securing procedure wherein the tube proximate end 632 is inserted through the sheath distal neck end opening 627 (FIG. 18a), thus pushing an outer portion of the sheath 622 into the sheath passage 628 whereby the sheath 622 is doubled on itself. The resulting structure (FIG. 18b) can then be secured with ligatures 640 or other suitable, encircling fastening means or clamps to provide an extra measure of security against leakage, thereby enhancing the effectiveness of the vacuum source 638 and minimizing the risk of bacteria entering the wound site 602 along the suction tube 630.

The system 601 is adapted for the introduction of fluids as well as the evacuation thereof. Thus, various fluids such as antibiotics, growth factor, liquid medications, enzymes, etc. can be introduced to the wound site 602. Liquids can also be introduced to the wound site 602 for the purpose of irrigating the wound. Such liquids can be removed by using the wound dressing system 601 in a suction/drainage mode of operation. Multiple wound dressing systems 601 can be employed for simultaneous introduction and evacuation of fluids. The wound dressing system 601 can be used in tandem, or with multiple conduit means 610 for simultaneous fluid introduction and evacuation. The wound dressing system 601 is adapted for dressing a variety of wounds, particularly cavitary wounds, such as might result from a skin graft procedure at a donor location, a burn, a decubitus ulcer, etc. The wound dressing system 601 can be preassembled and prepackaged in various size and component material combinations, with the appropriate prepackage system being selected by the health care practitioner based upon the requirements for dressing a particular wound. Alternatively, the components can be assembled in situ, for example, in an operating room or in a health care facility, by the health care practitioner. The size relationships of the various components can vary according to the conditions of particular wounds being dressed. For example, the fluid control means 608 can be relatively large and the panel means 606 can be relatively small for placement at any one of a variety of locations on -the fluid control means 608. Possible configurations include placement of a relatively small panel means 606 at an edge of the fluid control means 608, placement of a relatively small panel 606 at or near the center of a relatively large fluid control means 608 with the suction tube 630 extending through an opening in the fluid control means 608, etc.

IX. Suction Sponge System 701

Figures 18A, 18B, 19, 20, 21, 22, 23:
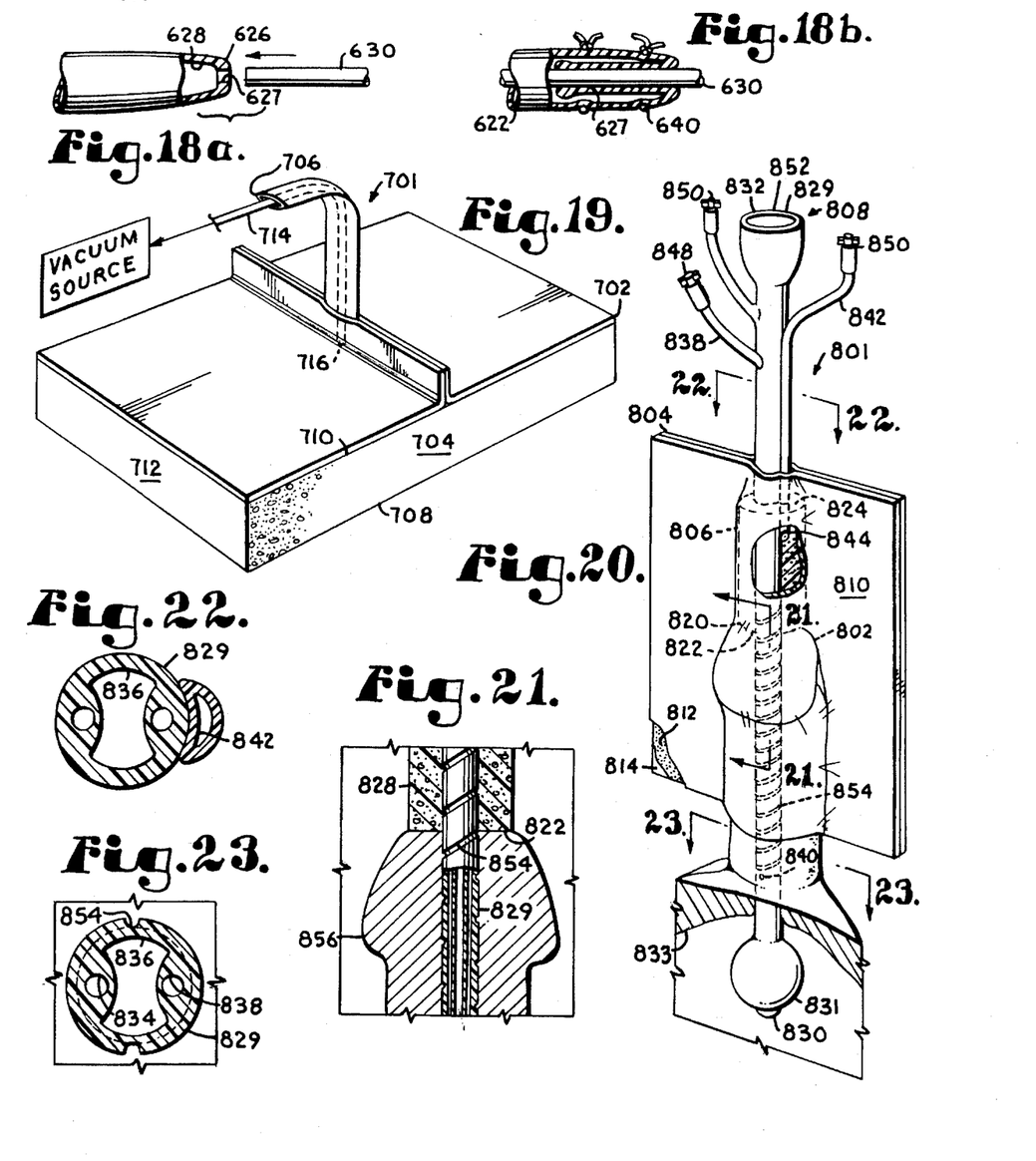
FIG. 18a is fragmentary, side elevational view thereof, particularly showing a suction tube proximate end prior to insertion into a sheath.
FIG. 18b is a fragmentary, side elevational view thereof, particularly showing the suction tube proximate end inserted into the sheath.
FIG. 19 is a top perspective view of a suction sponge system comprising an eighth modified or alternative embodiment of the present invention.
FIG. 20 is a perspective view of an extremity fluidic connection system comprising a ninth modified or alternative embodiment of the present invention.
FIG. 21 is an enlarged, fragmentary, cross-sectional view thereof, taken generally along line 21—21 in FIG. 20.
FIG. 22 is an enlarged, fragmentary, cross-sectional view thereof, taken generally along line 22—22 in FIG. 20.
FIG. 23 is an enlarged, fragmentary, cross-sectional view thereof, taken generally along line 23—23 in FIG. 20.
Figure 24:
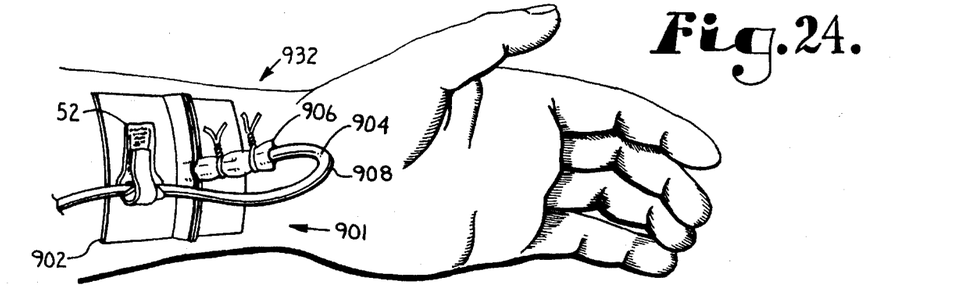
FIG. 24 is a perspective view of an intravenous tube system including a cinch loop fastener comprising a tenth modified or alternative embodiment of the present invention.

A suction sponge system 701 comprising an eighth modified or alternative embodiment of the present invention is shown in FIG. 19. The suction sponge system 701 generally comprises panel means 702, sponge means 704 and conduit means 706. The sponge means 704 can assume various configurations to accommodate the requirements of particular applications. The sponge means 704 as shown in FIG. 19 is generally rectangular in form, with inner and outer sponge faces 708, 710, and a perimeter edge 712.

Without limitation on the generality of useful sponge materials, exemplary sponge materials include "Merocel", and materials available from ASSI, Wick, Dow-Corning-Wright, Axiom Medical Products, Inc. and Davol, Inc. subsidiary of C. R. Bard, Inc. Such materials are preferably chosen for their desired characteristics such as capillary action, porosity, etc. Such products, which include a variety of foams, can be provided with an anti-clotting or anti-coagulation coating. Mat materials, such as polyurethane foam, may be suitable for use with the suction sponge system 701.

The panel means 702 is affixed to the sponge outer face 710, and can comprise panel means such as the panel means 606 described above. The conduit means 706 can be substantially similar to the conduit means 610 described above.

The suction sponge system 701 can be utilized in a variety of surgical and other medical procedures where fluid evacuation is desired. In particular, the suction sponge 701 combines the benefits of open-ended suction tubes and surgical sponges by providing a system for evacuating fluid from a relatively wide area.

The panel means 702 and the sponge means 704 can be modified in the operating room and matched to meet the requirements of various applications. For example, they can be trimmed to accommodate the sizes and shapes of various wounds and operating sites.

A suction tube 714 preferably has a proximate end 716 thereof located in close proximity to the outer sponge face 710 for enhancing the collection of fluid from the sponge means 704. The suction tube proximate end 716 can be positioned at various locations on the sponge outer face 710, but a central location may be preferable to provide the shortest average distances for fluid flow from the sponge outer face 710 and the sponge perimeter edge 712.

X. Extremity Fluidic Communication System 801

A fluidic connection system comprising a tenth modified or alternative embodiment of the present invention is shown in FIGS. 20–23 and is generally designated by the reference numeral 801. The fluidic communication system 801 is designed for application to an extremity (e.g., a penis) 802 and generally comprises panel means 804, fluid control means 806 and conduit means 808.

The panels means 804 can comprise, for example, any suitable membrane or sheet-type material, such as those discussed above, which can be affixed to the extremity by placing a panel section 810 on each side thereof as shown, with adhesive 812 on inner surfaces 814 of the panel sections 810 securing them together. Alternatively, the panel means 804 can be wrapped around an extremity and secured with other fixation means, such as tape, sutures, etc.

The fluid control means 806 comprises a collar 820 of a suitable sponge material (see the discussion above) with a generally cylindrical configuration having proximate and distal ends 822, 824 and a collar bore 826 extending therebetween and open thereat. The collar 820 includes a slit 828 extending longitudinally between its ends 822, 824 for providing access to the collar bore 826 whereby the collar 820 can be snapped in place over the conduit means 808.

The conduit means 808 comprises a multi-lumen catheter tube 829 with a proximate end 830 having a collector balloon 831 for inflation within the bladder 833 of a patient and a distal end 832. The catheter tube 829 includes an air lumen 834 in communication with the balloon 831 for inflating same, a urine lumen 836 which extends generally axially from the balloon 831, an irrigation lumen 833 which terminates at an irrigation outlet 840 in spaced relation outwardly from the proximate end 830, and a suction lumen 842 which terminates at a suction port 840 which can be located in proximity to the collar distal end 824 in fluidic communication with the collar 820. The air, irrigation and suction lumens 834, 838 and 842 can be provided with suitable connectors 846, 848, 850 respectively, e.g., "Luer-Lock" type connectors for fluidic connection to suitable fluidic devices (e.g., pneumatic squeeze bulbs, collection bags, pumps and suction sources) which are commonly used for these purposes. The urine lumen 836 terminates at a bell-shaped female end 852 which can be connected to a suitable collection bag via a tube.

A spiral groove 854 is formed in the catheter tube 829 and extends generally from the area of the irrigation outlet 840 to the suction port 844 and provides a passageway for irrigating fluid which can be introduced through the irrigation lumen 838 and evacuated through the suction lumen 842 and generally functions to irrigate and flush the urethra, thereby reducing risks of infection and bacteriological activity in the urethra.

The collar 820 is preferably installed with its proximate end 822 against the meatus 856. Various configurations of the conduit means 808 can be employed, for example, the irrigation lumen 838 can be eliminated. The extremity fluidic connection system 801 can be utilized to treat other extremities, such as hands, arms, feet, legs, digits, etc. Suitable panel means 804, fluid control means 806 and conduit means 808 can be selected for particular applications.

XI. Cinch Loop Fastener 52

A cinch loop fastener 52 as shown in FIGS. 6 and 9.is shown in an intravenous tube system 901 in FIGS. 24–30 as a tenth modified or alternative embodiment of the present invention. The IV tube system 901 includes panel means 902, conduit means 904 comprising a sheath 906 and an intravenous tube 908, and the cinch loop fastener 52. The discussions of panel means and the conduit means above pertain to the panel means 902 and the conduit means 904, which can assume various configurations and comprise various materials within the scope of the present invention.

Figure 25:
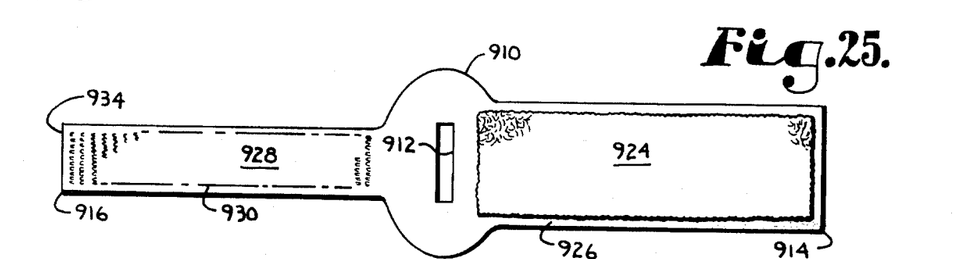
FIG. 25 is a top plan view of the cinch loop fastener in an open position thereof.
Figures 26, 27, 29:
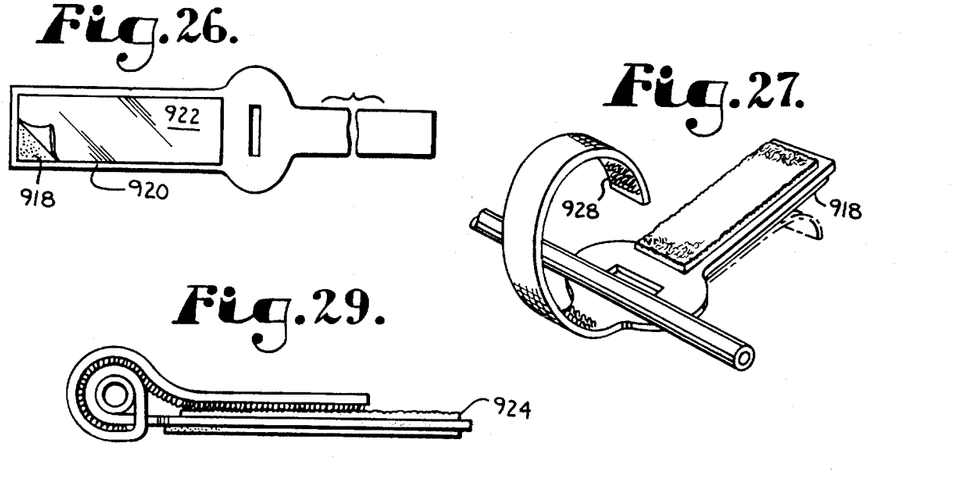
FIG. 26 is a bottom plan view of the cinch loop fastener.
FIG. 27 is a perspective view of the cinch loop fastener showing a preliminary stage of fastening to an IV tube.
FIG. 29 is a side elevational view of the cinch loop fastener, shown fastened to the IV tube.
Figure 28:
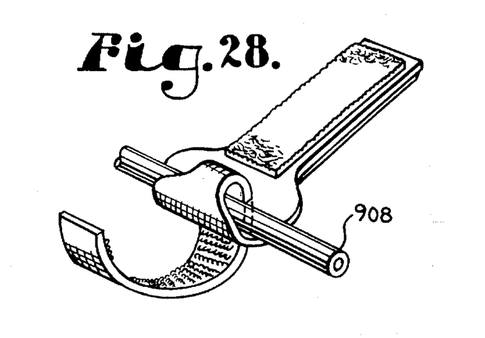
FIG. 28 is a perspective view of the cinch loop fastener, showing an intermediate stage of fastening to the IV tube.
Figure 30:
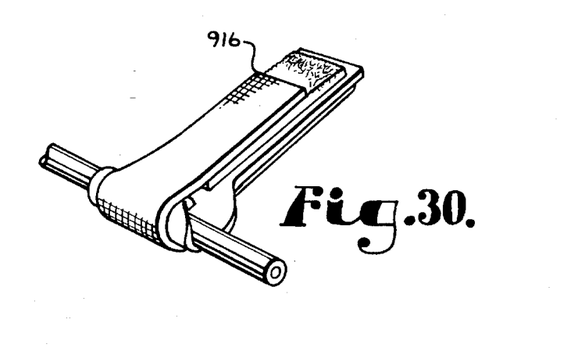
FIG. 30 is a perspective view of the cinch loop fastener, shown fastened to the IV tube.

The cinch loop fastener 52 includes a hub 910 with a generally oval configuration and a slot 912, a relatively wide base leg 914 and a relatively narrow wrap leg 916. Adhesive 918 can be applied to a base leg outer surface 920 and covered by a removable, protective adhesive cover 922. A loop or pile portion 924 of the hook-and-loop fastener 54 (e.g., "Velcro" fastener) can be applied to an inner surface 926 of the base leg 920 and a hook portion 928 thereof can be applied to an inner surface 930 of the wrap leg 916.

FIGS. 27–30 show wrapping the IV tube 908 with the wrap leg 916 and securing the cinch loop fastener 52 in its closed configuration adhered to the panel means 902 over an IV site 932. These steps involve extending a distal end 934 of the wrap leg 916 through the slot 912, returning the wrap leg 916 outwardly from under the hub 910, and folding the wrap leg 916 back over the base leg 914 for attachment of the hook-and-loop fastener 54. The wrap leg 916 thus pivots around the hub 910 through about one and one-half turns, or about 540 degrees.

The cinch loop fastener 52 can be used for securing a variety of tube and sheaths on a variety of surfaces, including panels, dressings and fasteners such as those described herein.

It is to be understood that while certain forms of the present invention have been illustrated and described herein, it is not to be limited to the specific forms or arrangement or parts described and shown.

What is claimed and desired to be secured by Letters Patent is as follows:

1. A method for treating surface wounds such as burns, pressure ulcers and skin graft donor sites, comprising the steps of:
   (a) apply a dressing to the wound, said dressing including:
      (i) a foam section covered and sealed by an adhesive polymer sheet; and
      (ii) a flexible suction tube in fluid communication with said foam section;
   (b) adhesively applying said adhesive polymer sheet to said foam section;
   (c) providing a motorized pump;
   (d) fluidically connecting said motorized pump to said suction tube;
   (e) applying negative pressure to the wound through the tube by use of said motorized pump and
   (f) directing fluid from said surface wound through said foam section by said polymer sheet.

* * * * *